United States Patent [19]

Vara et al.

[11] Patent Number: 4,766,252

[45] Date of Patent: Aug. 23, 1988

[54] SOLVENT AND STAIN RESISTANT COATINGS

[75] Inventors: Fulvio J. Vara, Chester; Lowell R. Anderson, Morristown; James A. Dougherty, Prospect Park, all of N.J.

[73] Assignee: GAF Corporation, Wayne, N.J.

[21] Appl. No.: 109,676

[22] Filed: Oct. 16, 1987

[51] Int. Cl.$^4$ .................... C07C 43/16; B05D 3/06
[52] U.S. Cl. .................... 568/616; 568/673; 427/44; 549/260
[58] Field of Search .................... 568/616, 673

[56] References Cited

FOREIGN PATENT DOCUMENTS 621813  6/1961  Canada .................... 568/616

Primary Examiner—Howard T. Mars

Attorney, Agent, or Firm—Marilyn J. Maue; Joshua J. Ward

[57] ABSTRACT

This invention relates to rapidly curable, non-degradable protective coating compositions containing a divinylether alkene having the formula

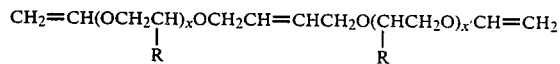

wherein R is hydrogen or methyl and x and x' are integers each having a value of from 0 to 24, a cross-linkable base resin and a catalytic amount of a cross-linking initiator; and to the preparation and use of the above divinylether alkenes for metal or plastic coatings which possess high resistance to solvents and improved flexibility.

1 Claim, No Drawings

SOLVENT AND STAIN RESISTANT COATINGS

In one aspect this invention relates to novel compounds of the vinylether alkene type In another aspect the invention relates to the preparation of said vinylether alkenes and in a third aspect the invention pertains to the use of said vinylether alkenes as a protective coating in formulations for metal and plastic materials

BACKGROUND OF THE INVENTION

Many formulations have been proposed for coating metal and plastic surfaces, including polyepoxy compounds such as the cycloaliphatic diepoxides and glycol ethers These compounds are generally formulated in solvents or emulsified with water and reacted with typical epoxy hardeners such as epoxy polyamides, polyamines, anhydrides, melamines, imidazoles and acids However, these formulations pollute the atmosphere since the solvent must be evaporated in order to form a usable coating. The alternative of solvent recovery is found to be uneconomical and therefore not practiced Water emulsified epoxy coatings also require evaporation which, due to the high heat of water vaporization, is also uneconomical and difficult to drive to completion. To avoid these disadvantages, the use of a solvent free coating formulation comprising a cross-linkable base resin, a cycloaliphatic epoxy compound and a cross-linking initiator has been proposed Although such a formulation would be acceptable from an economical and environmental standpoint, it is known that the cycloaliphatic epoxy compounds react slowly with the polyepoxy resin resulting in a lack of resistance to common polar solvents such as methyl ethyl ketone, acetone, alcohols, etc. Still further, the polyepoxy compounds produce brittle coatings unless substantial amounts of a flexibilizing agent, such as tripropylene glycol is added to the formulation.

Another deficiency of the above formulated compounds is their inability to accept high levels of pigment loading before an unmanageable viscosity is reached.

Accordingly, it is an object of this invention to overcome the deficiencies of the prior metal and plastic coatings described above.

Another object of this invention is to provide a flexible coating suitable for thin layer application which shows high resistance to chemical solvents.

Still another object of the invention is to provide a formulation which will accept a high level of pigment loading and which possesses good wear resistance for lettering and designs which may have been printed under the coating.

Another object is to provide an economical and commercially feasible method for preparing the compounds of the present invention.

Yet another object is to provide new and novel compounds of the vinylether alkene type.

THE INVENTION

According to this invention there is provided novel protective compositions suitable for coating on metal or plastic substrates which comprise an organic cross-linking initiator, a cross-linkable base resin and a divinylether alkene having the formula:

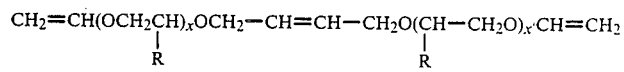

wherein R is hydrogen or methyl and x and x' have a value of from 0 to 24. The divinylether alkenes wherein x and x' are positive integers are novel and possess lower volatility while their cross-linked products are significantly more flexible, depending on the number of alkyleneoxy groups contained in the monomer chain. Of the alkoxylated divinylether alkenes, those wherein x and x' have a value of from 0 to 4 are preferred and those wherein the alkyleneoxy groups are ethyleneoxy groups, as well as the compound where x and x' are zero, are most preferred for coating purposes The compounds of this invention can be prepared by a transvinylation reaction according to the general formula

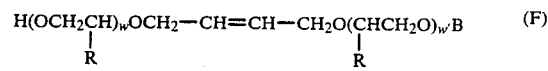

+ a coreactant high boiling mono- or polyvinyl ether reactant having the structure G or H.

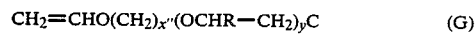

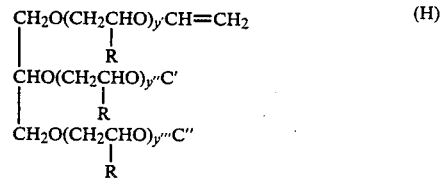

wherein B is —H or —CH=CH$_2$; C, C' and C'' are each hydrogen, C$_1$ to C$_4$ alkyl, C$_1$ to C$_4$ alkoxy or —(CH$_2$)$_{x''}$OCH=CH$_2$ when B is —CH=CH$_2$ and C and at least one of C' and C'' are —(CH$_2$)$_{x''}$OCH=CH$_2$ when B is hydrogen; x'' is an integer having a value of from zero to 4; R is hydrogen or methyl; y is an integer having a value of from 3 to 5; y', y'' and y''' are integers the sum of which is from 4 to 24, and w and w' are integers having a value of from 0 to 24. In compound (H) it is essential that the vinyl groups be separated by more than 4 carbon atoms. If they are not, the monovinylated compound may undergo internal addition of the hydroxy group to the vinyl group and form a 5 or 6 membered ring; thus failing to provide the desired divinylated product and destroying the cross-linking potential of the vinyl group.

The hydroxy terminated reactant (F) is mixed with the vinyl ether coreactant (G) or (H) in an amount at least sufficient to convert all of the hydroxy sites in compound (F) to vinyl ether groups. More specifically, a ratio of hydroxy group to vinyl ether group between about 1:1 and 1:5, preferably 1:1.5 to 1:3 for each hydroxylated site in reactant (F) at which transvinylation is to be effected, can be employed. These coreactants are required to have low volatility so that they will not be vaporized under the ensuing reaction conditions. Preferred coreactants have a volatility less than 55° C. at 1.5 mm Hg and a boiling point greater than 250° C. A soluble mercury salt catalyst, between about 1 and about 10% of the total mixture is added to initiate the reaction Although mercuric acetate is the preferred catalyst, other mercury compounds such as mercuric sulfate, mercuric nitrate, and mercuric chloride may be substituted in whole or in part to induce transvinylation. The resulting mixture is then reacted at a temperature between about 25° C. and 250° C., preferably between about 60° C. and about 150° C. and below the decomposition temperature of compound (F) and then vacuum distilled. The distillation pressures employed may range between about 0.5 and about 50 mm Hg, preferably between about 1 and about 10 mm Hg.

about 40° C. and about 100° C. Close temperature control is particularly important in the production of each of the divinylether alkene products since there is a very small difference in boiling point between the product and the unreacted alcohol component.

The most preferred product of the present reaction may be represented as follows.

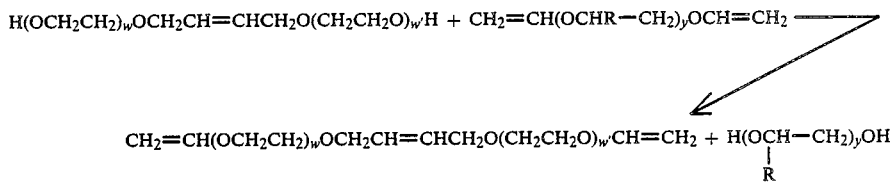

wherein w and w' have a value of from 0 to 4 and the mole ratio of hydroxyl group to vinyl moiety is between about 1:1 and about 1:2.

The general reation can be expressed by the equation:

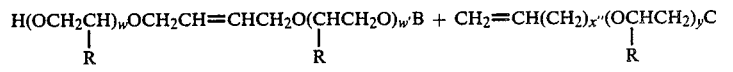

(G)

or

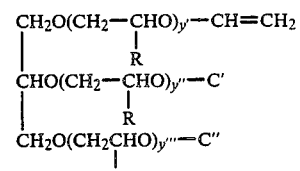

(H)

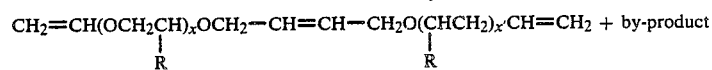

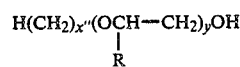   or   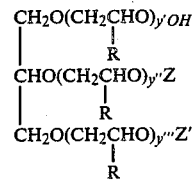

(J.)   (K.)

In a batch process, the reaction is conducted over a period of from about 1 to about 3 hours; however, the process may be carried out under continuous conditions or with intermittent product removal. In either case the product draw-off shifts the equilibrium of the product lean reaction mixture to the production of more product Thus, to maximize product yield, the distillatior can be halted and the reaction mixture allowed to re-equilibrate for about 5 to 30 minutes, after which the distillation and product take-off is resumed and additional product collected. This operation can be repeated several times to drive the reaction toward completion.

The desired product and a small amount of hydroxy ether by-product withdrawn from the reaction zone is subjected to closely controlled fractional distillation using from 10 to 30 plates, preferably from 12 to 25 plates under vacuum and at a temperature between wherein each of Z and Z' is independently vinyl, hydroxy, or the same as C' and C" depending on the transvinylation (—OH) sites in the alcoholic reactant (F) and the terminal groups in the coreactant (H); w and w' have a value of from 0 to 24 and B, C, C', C", R, x, x', x", y, y', y" and y''' are as defined above.

The product of the above reaction is obtained in at least 80% purity and can be further purified. Although purification of product may be required for some uses, e.g. in medicinal or cosmetic uses, removal of by-product to levels below about 15% is usually not required.

The alkoxylated divinylether alkenes of the present invention can also be prepared by direct vinylation wherein the alkoxylated butenediol and an alkali metal hydroxide catalyst, e.g. KOH or NaOH, are introduced into an autoclave, the autoclave is purged with nitrogen and pressured to about 100 pounds with acetylene. The reaction is effected at about 150° C. for a period of from about 6 to 8 hours after which the autoclave is opened and the liquid contents distilled under a vacuum of from about 1 to about 10 mm Hg to recover the alkoxylated divinylether alkene product.

The products obtained can be directly formulated into a composition suitable for coating metal or plastic surfaces. As can be seen from the product structural formula, the present compounds have high cross-linking capability which takes place at the multiple unsaturated sites and are characterized by rapid curability by heat or radiant energy. It has been found that the speed of curing for formulations containing the present compounds is seven times faster than those consisting of epoxides. The present compounds possess high adhesion to metals such as for example aluminum surfaces and impart excellent abrasion resistance. A surface protected with this compound in a cross-linkable formulation is provided with a pigment loadable coating which can be used on plastic food bags or metal cans and one which is resistant to solvent deterioration. These coatings also protect against metal corrosion. Another important advantage realized by the incorporation of the present alkyleneoxy divinylether alkenes is their ability to impart flexibility to the coating material so that no extraneous flexibilizing agent need be added to the coating composition.

A principal advantage of the alkoxylated divinylether alkenes wherein x has a value of from about 0 to about 4 over others is their resistance to common solvents including ketones, alcohols, esters and aromatic solvents. As the value of x increases, the coatings in which the compound is formulated become more flexible; although somewhat lowered in solvent resistance.

Generally coating compositions of the present invention include between about 30 wt. % and about 55 wt. % of the present compound; between about 65 wt. % and about 45 wt. % of an adhesive base resin such as an epoxy resin or a cyclo aliphatic epoxide; between about 0.5 wt. % and about 8 wt. % of a cross-linking initiator and between about 0 and about 3 wt. % of a surfactant. The base resins of the present compositions are cross-linkable components which impart adhesion and hardness to the composition and are preferably those which contain one or more epoxy and/or olefinically unsaturated groups. Suitable examples of such compounds include diglycidyl ethers of bisphenol A having an epoxy equivalent weight between about 150 and about 10,000, polyglycidyl ethers of phenol formaldehyde novolak, and cycloaliphatic epoxides, and the like. Also, a non-reactive resin such as a saturated polyester or carbohydrate can be used.

The present compound is mixed at a temperature of from about 20° C. to about 50° C. under atmospheric pressure with the adhesive base resin in a mole ratio of between about 20:80 and about 80:20, preferably in a mole ratio of from about 35:65 to about 65:35 until a homogeneous mixture is obtained The surfactant and the photoinitiator are then added to the resulting mixture which can be then coated on a surface such as a surface of aluminum, steel, chromium, copper, tin-plate, brass, bronze, tin-free steel as used in cans for beer or beverages or on a plastic substrate such as a surface of polyester, polystyrene, acrylic polymer and the like.

Suitable photoinitiators used to induce cross-linking between the vinyl ether and the base resin include triphenyl sulfonium hexafluorophosphate, fluoroarcynate, fluoroantimonate, diazonium salts, aryl ferrocene and fluorophosphate. Generally, for radiation curing, deblockable acids such as onium salts, iron-arene complexes or para-toluene sulfonic acid complexes can be employed as cross-linking initiators For thermoset curing, boron trifluoride complexes, para-toluene sulfonic acid complexes and trifluoromethane sulfonic acid complexes are particularly recommended.

The composition containing the present vinyl ether, the base resin, the cross-linking initiator and optionally surfactant, is coated on a substrate in a thickness between about 0.02 and about 30 mils, preferably between about 0.1 to 3 mils and most preferably between about 0.2 to 1 mil. In radiation curing, the coated substrate is rapidly cured to a tack-free state at an energy for light radiation of between about 0.15 joules/cm$^2$ and about 225 joules/cm$^2$, preferably between about 6 joules/cm$^2$ and about 105 joules/cm$^2$. For electron beam radiation, an energy of between about 0.1 and about 5 megarads are employed. Any source of radiation curing can be employed for the present process. Rapid transformation to a tack free state is particularly important on continuous coating lines in order that tack free parts can be conveniently unloaded and stacked or fabricated before post baking. Vinyl ether formulations become tack free about 7 times faster than epoxy formulations (about 700 feet/minute vs. about 100 feet/minute).

After the tack-free state is achieved, the curing is completed by a post-bake for a period of from about 2 to about 20 minutes at a temperature of from about 50° to about 200° C., preferably from about 5 to about 15 minutes at a temperature of from about 125° to about 175° C.

When curing speed is not important, a thermoset process can be employed. In this process, merely heating to between about 25° C. and about 250° C., preferably between about 50° C. and about 200° C., for a period of 5 to about 30 minutes in the presence of a strong acid, e.g. trifluoromethyl sulfonic acid or any of those mentioned above, is sufficient to provide a tack-free protective coating.

The present formulations function as reactive diluents when used with printing ink, pigment and the like. These coloring materials are uniformly dispersed in the coating mix, applied in a predetermined pattern in one or more colors and in one or more applications and then subjected to curing as described above. During curing the coating is internally cross-linked at the unsaturated sites. Under optimum conditions with preferred initiators, the present composition is capable of immediate cure such that 700 feet per minute of film can be cured to a tack-free condition. Such rapidity in curing represents a great improvement over prior UV curable epoxy compositions which require at least 1 minute per 100 feet of film. Because of the alkoxylation, the coatings also exhibit a high degree of flexibility which may be enhanced by the presence of alkyleneoxy groups lacking from other somewhat related compositions and have improved substrate substantivity, as well as excellent solvent resistance.

Having thus generally described the invention, reference is now had to the following Examples. However it is to be understood that the scope of this invention is not intended to be limited to these embodiments but is extended to the general discussion above with modifications and alterations normally apparent to the skilled artisan and to the appended claims.

EXAMPLE 1

Into the pot of a 15 plate Oldershaw distillation column was introduced 52 g. of 2-butene-1,4-diol, 115 g. of triethylene glycol divinyl ether, $$CH_2=CHO(CH_2CH_2O)_3CH=CH_2$$

and 10 g. of mercuric acetate. The mixture was heated to a pot temperature of 85° C. for a few minutes and a first cut of 12.6 g. of product having the formula $$CH_2=CHOCH_2-CH=CH-CH_2OCH=CH_2$$

was distilled off and collected in a few minutes within a 3° temperature range including 68° C. under a pressure of 1.5 mm Hg. The distillation was discontinued and the reaction mixture was allowed to stand for a period of 15 minutes during which the reaction mixture re-equilibrated. The distillation under the above conditions was then resumed. This incremental draw-off of product was repeated 3 times and product collected in an overall yield of 75% and 80% purity. The product contained a minor amount of by-product having the formula $H(OCH_2CH_2)OH$ and was identified by gas chromatography, NMR and infrared spectrum.

EXAMPLE 2

Example 1 is repeated, except that the 205 g. of the propoxylated coreactant $$CH_2=CH(OCH_2CH)_{Av.4}OCH=CH_2$$
$$|$$
$$CH_3$$

is substituted therein. The same product as in Example 1 in about the same amount and purity is obtained; however, the by-product in this case is the corresponding propoxylated diol derivative, $$H(OCH_2CH)_{Av.4}OH.$$
$$|$$
$$CH_3$$

EXAMPLE 3

Example 1 is repeated, except that 68 g. of 1-hydroxy-4-vinyl-butene-2 was reacted with 880 g. of an ethoxylated mono vinyl glycerol having the formula $$CH_2O(CH_2CH_2O)_{20}CH=CH_2$$
$$|$$
$$CHO(CH_2CH_2O)_{20}CH=CH_2$$
$$|$$
$$CH_2O(CH_2CH_2O)_{20}CH=CH_2$$

The corresponding product, $$CH_2=CH(OCH_2CH_2)_{20}OCH_2CH=CHC-$$
$$H_2O(CH_2CH_2O)_{20}CH=CH_2,$$

in about the same amount and purity as in Example 1 is obtained; however the by-product in this case is the corresponding ethoxylated glycerol derivative.

Example 1 is repeated except that 502 g. of $$H(OCH_2CH_2)_{12}OCH_2CH=CHCH_2O(CH_2C-$$
$$H_2O)_{12}H$$

is substituted for 52 g. of 2-butene-1,4-diol. The distillation product of the reaction, $$CH_2=CH(OCH_2CH_2)_{12}OCH_2CH=CHC-$$
$$H_2O(CH_2CH_2O)_{12}CH=CH_2$$

is obtained in at least 70% purity and the by-product of the reaction is the same as that obtained in Example 1.

EXAMPLE 5

Two commercial coating formulations (No. 1 and No. 2) and a formulation of the present invention (No. 3) were prepared and compared. The components of these compositions are shown in following Table I. All amounts are reported as wt. %.

TABLE I

| COMPOSITION NO. 1 | COMPOSITION NO. 2 | COMPOSITION NO. 3 |
|---|---|---|
| 52% cycloaliphatic epoxide (1) | 56.9% divinyl compound (6) | 56.7% vinyl epoxy ether (7) |
| 18.5% Bisphenol A epoxide (Epon-834) (2) | 39.4% Bisphenol A epoxide (Epon-834) | 38.6% Bisphenol A epoxide (Epon-834) |
| 25% tripropylene glycol (3) | 3.3% sulfonium salt initiator (4) | 3.3% sulfonium salt initiator (4) |
| 4.0% sulfonium salt initiator (4) | 0.41% fluorochemical surfactant (5) | 0.41% fluorochemical surfactant (5) |
| 0.5% fluorochemical surfactant (5) | | |

(1) 3,4-epoxycyclohexylmethyl-3'4'-epoxycyclohexane carboxylate (cross-linking agent)
(2) an epoxy resin based on Bisphenol A having an epoxy equivalent weight between about 180 and 6,000 (provides adhesion & strength)
(3) this composition required a substantial amount of flexibilizer to prevent cracking
(4) triphenyl sulfonium hexafluorophosphate
(5) fluorinated alkyl alkoxylates (Fluorochemical 171 supplied by Minnesota Mining & Manufacturing Co., St. Paul, Minnesota)
(6) triethylene glycol divinyl ether crosslinking agent
(7) diethoxylated-2-butene-1,4-diol divinyl ether crosslinking agent of Example 1

The above formulations were individually coated on aluminum panels by hand draw-down using a number 3 Mayer bar to give a coating thickness of about 6.5 microns. The panels were then subjected to a UV light exposure of approximately 15 joules/cm² by passing them under two 200 watt/inch UV lamps at 100 feet/minute. This was followed by a thermal bake at 177° C. for 10 minutes The coatings were then subjected to a Boiling Water Immersion Test a solvent resistance test and a reverse impact test. For the water immersion, the coated panel was immersed in boiling water for 30 minutes, after which it was removed, dried and subjected to adhesion test ASTM D-3359-K-B.

For the solvent resistance test, a methylethyl ketone saturated cheesecloth was rubbed across the surface of the coated panel under a constant pressure. The number of back and forth strokes needed to break through the coating was recorded. The reverse impact test was carried out by placing a coated panel face down on a die containing a 0.640 inch hole. A 0.625 inch pin with rounded tip was placed on the back of the panel directly over the hole. A 1 lb. weight was dropped, from varying heights, onto the pin causing rapid deformation of the panel and coating and the coating was examined for cracking or crazing. The maximum energy the coating can absorb before failure was recorded. The results of these tests are reported in following Table II.

TABLE II

| TEST | COMPOSITIONS | | |
|---|---|---|---|
| | 1 | 2 | 3 |
| Adhesion | 100 | 100 | 100 |
| Water Submersion | 100 | 100 | 100 |
| Solvent Resistance | 2 | 5 | 19 |
| Reverse Impact (lbs. at failure) | <8 | 24 | 24 |

In addition to the above results, it was found that Composition No. 3 was significantly less viscous than Composition 1. Accordingly, thin films of the type shown in Composition 3, suitable for coating magnetic tapes and other recording media, could be produced. This property, together with the markedly increased flexibility and solvent resistance of compositions incorporating the present divinyl ether alkenes, render them excellent candidates for coating electron beam recording films and wire like filaments.

EXAMPLE 6

Example 5 was repeated except that 2-butene-1,4-divinylether was substituted for compound 7 in Composition No. 3 (Compositions 4, 5 and 6 below corresponding to 1, 2 and 3 respectively in Example 5). The 6.5 micron coatings on aluminum panels were subjected to the adhesion, boiling water submersion reverse impact and solvent resistance tests described above and the results are reported in following Table III.

TABLE III

| Test | Composition | | |
|---|---|---|---|
| | 4 | 5 | 6 |
| Adhesion | 100 | 100 | 100 |
| Water Submersion | 100 | 100 | 16 |
| Solvent Resistance | 2 | 5 | 70 |
| Reverse Impact | <8 | 24 | 32 |

EXAMPLE 7

Example 6 was repeated with the same formulations except that the percent sulfonium salt initiator was reduced to 1.5 wt. % (Compositions 7, 8 and 9 below corresponding to 4, 5 and 6 respectively) Coatings of 6.5 microns were applied to aluminum panels as in Example 5 and were cured by an electron beam exposure of 1.5 Mrad. After a thermal bake of 10 minutes at 177° C. the coated panels were subjected to the same tests as set forth in Example 5. The results are as reported in Table IV.

TABLE IV

| Test | Composition | | |
|---|---|---|---|
| | 7 | 8 | 9 |
| Adhesion | 100 | 100 | 100 |
| Water Submersion | 100 | 100 | 100 |
| Solvent Resistance | 4 | 50 | 200 |

EXAMPLE 8

Example 6 was again repeated with the same formulations except that the sulfonium salt photoinitiator was replaced with 1.5 wt. % of the diethylammonium salt of trifluoromethanesulfonic acid (Compositions 10, 11 and 12 below corresponding to 4, 5 and 6 respectively). Coatings of 6.5 micron were applied on aluminum panels as in Example 5, were cured with a thermal bake of 15 minutes at 177° C. and the coatings subjected to the same tests as in Example 5. The results are as reported in following Table V.

TABLE V

| Test | Composition | | |
|---|---|---|---|
| | 10 | 11 | 12 |
| Adhesion | 100 | 100 | 100 |
| Water submersion | 100 | 100 | 100 |
| Solvent resistance | 3 | 25 | 200 |
| Reverse Impact | <8 | 18 | 24 |

EXAMPLE 9

The cure speed in feet per minute and number of seconds to achieve a tack free conditions of coating compositions 1-6 reported in Examples 5 and 6 above, were calculated. The tack free state was determined by non-adhesion after touching the coated surface with a cottonball. The results of this determination are reported in following Table VI.

TABLE VI

| | Coating Composition | | | | | |
|---|---|---|---|---|---|---|
| | 1 | 2 | 3 | 4 | 5 | 6 |
| cure speed | 100 | 700 | 700 | 100 | 700 | 700 |
| tack free time | 60 | <1 | <1 | 60 | <1 | <1 |

Many alterations and variations of the above description and disclosure will become apparent to those skilled in the art. However, it is intended that such modifications and alterations be included within the scope of this invention.

What is claimed is:

1. An alkoxylated divinylether alkene compound having the formula.

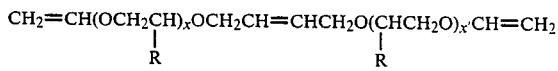

wherein x and x' are integers each having a value of from 1 to 24 wherein R is hydrogen or methyl.

* * * * *